(12) United States Patent
Kuromiya et al.

(10) Patent No.: US 7,696,375 B2
(45) Date of Patent: Apr. 13, 2010

(54) METHOD FOR PRODUCING LACTIC ACID ESTER

(75) Inventors: Shigeru Kuromiya, Nagoya (JP); Osamu Saotome, Nissin (JP); Ikuo Yamaguchi, Okazaki (JP); Kazunori Habu, Toyota (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 15 days.

(21) Appl. No.: 11/995,864

(22) PCT Filed: Jun. 27, 2006

(86) PCT No.: PCT/JP2006/313177

§ 371 (c)(1),
(2), (4) Date: Jan. 16, 2008

(87) PCT Pub. No.: WO2007/013259

PCT Pub. Date: Feb. 1, 2007

(65) Prior Publication Data

US 2009/0105501 A1 Apr. 23, 2009

(30) Foreign Application Priority Data

Jul. 27, 2005 (JP) ............................. 2005-217749

(51) Int. Cl.
*C07C 69/66* (2006.01)
(52) U.S. Cl. ..................................... 560/179
(58) Field of Classification Search ........................ None
See application file for complete search history.

(56) References Cited

U.S. PATENT DOCUMENTS

| 2,722,541 A | 11/1955 | Schulz, Jr., et al. |
| 5,453,365 A | 9/1995 | Sterzel et al. |
| 2002/0132967 A1 | 9/2002 | Ohara et al. |

FOREIGN PATENT DOCUMENTS

| DE | 43 41 770 A1 | 6/1995 |
| EP | 0 614 983 A2 | 9/1994 |
| JP | 6-311886 | 11/1994 |
| JP | 7-194387 | 8/1995 |
| JP | 10-287668 | 10/1998 |
| JP | 2002-300898 | 10/2002 |
| JP | 2003-284580 | 10/2003 |
| JP | 2004-208501 | 7/2004 |

OTHER PUBLICATIONS

Filachione, et al. "Preparation of Esters by Reaction of Ammonium Salts with Alchols", XP-002201046, Journal of the American Chemical Society, American Chemical Society, vol. 73, pp. 5265-5267, (Nov. 1951).

*Primary Examiner*—Paul A Zucker
(74) *Attorney, Agent, or Firm*—Finnegan, Henderson, Farabow, Garrett & Dunner, LLP

(57) ABSTRACT

This invention provides a method for producing a lactic acid ester that can minimize input energy at the time of production, that can reduce chemical costs, and that can minimize equipment costs. This method comprises steps of: performing an esterification reaction in a reaction solution containing ammonium lactate obtained via fermentation and alcohol with an ammonia concentration of 1.0% by weight or lower; and recovering the lactic acid ester synthesized in the above step.

3 Claims, 3 Drawing Sheets

METHOD FOR PRODUCING LACTIC ACID ESTER

TECHNICAL FIELD

The present invention relates to a method for producing a lactic acid ester wherein a target lactic acid ester is recovered from ammonium lactate obtained via fermentation.

BACKGROUND ART

A fermentation process whereby lactic acid is synthesized by fermentation caused by lactic acid bacteria, ammonium lactate is obtained therefrom, and a lactic acid ester is then produced is known as a method for producing a lactic acid ester (JP Patent Publication (Unexamined) Nos. 2004-208501, 2002-300898, 7-194387 (1995), and 2003-284580). In this method, lactic acid produced by fermentation is neutralized with ammonia to prepare ammonium lactate, and alcohol is added thereto to esterify the ammonium lactate. Also, sulfuric acid is added to the reaction system to promote the esterification reaction. In such a production method, a lactic acid ester contained in the reaction solution is isolated by distillation and recovered at the end of the process.

Conventional methods for producing a lactic acid ester, such as those disclosed in the above patent documents, do not provide techniques that are sufficient to industrially produce a lactic acid ester. These methods have not been practical in terms of production cost. Specifically, the industrial production of a lactic acid ester requires a minimization of input energy at the time of production, a reduction in chemical costs, and a minimization of equipment costs. However, conventional methods for producing a lactic acid ester have not been able to provide any concrete means of fulfilling such requirements.

DISCLOSURE OF THE INVENTION

Under the above circumstances, the present invention is intended to provide a cost-effective method of production of a lactic acid ester. More particularly, the present invention is intended to provide a method for producing a lactic acid ester that can minimize input energy at the time of production, that can reduce chemical costs, and that can minimize equipment costs.

The present inventors have conducted concentrated studies in order to attain the above objects. As a result, they discovered that input energy at the time of production can be minimized, that chemical costs can be reduced, and that equipment costs can be minimized by maintaining the ammonia concentration at a given level or lower in the reaction solution during the esterification reaction as part of the process of producing a lactic acid ester. This has led to the completion of the present invention.

Specifically, the present invention includes the following.

(1) A method for producing a lactic acid ester comprising steps of: performing an esterification reaction in a reaction solution containing ammonium lactate obtained via fermentation and alcohol with an ammonia concentration of 1.0% by weight or lower; and recovering the lactic acid ester synthesized in the above step.

(2) The method for producing a lactic acid ester according to (1), wherein the step of esterification further involves discharge of ammonia contained in the reaction solution to the outside of the reaction system with butanol vapor.

(3) The method for producing a lactic acid ester according to (2), wherein the step of esterification further involves completion of the reaction with a conversion rate that is 50% to 90% that attained at the esterification equilibrium.

(4) The method for producing a lactic acid ester according to (1), wherein the step of esterification involves addition of the liquid remaining after the recovery of the lactic acid ester to the reaction solution.

PREFERRED EMBODIMENTS OF THE INVENTION

Figure 1:
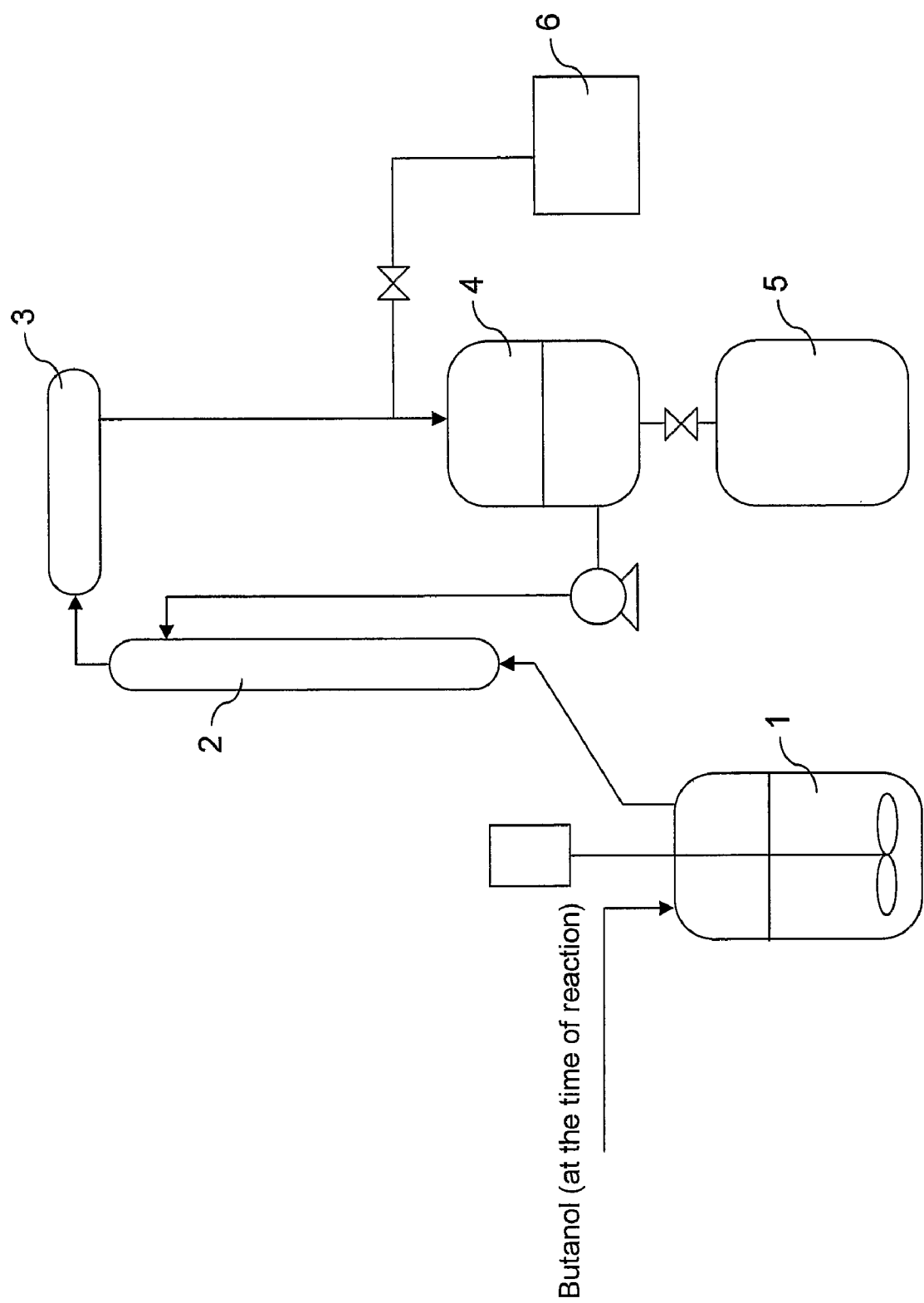
FIG. 1 shows an embodiment of the system for producing a lactic acid ester according to the present invention.

Hereafter, the method for producing a lactic acid ester according to the present invention is described in detail with reference to the drawings.

In the method for producing a lactic acid ester according to the present invention, a reaction solution containing ammonium lactate obtained by a so-called fermentation process is first used.

In the fermentation process, sugars contained in a medium are subjected to lactic acid fermentation with lactic acid-fermenting microorganisms. Bacteria, yeast, and molds can be used as such lactic acid-fermenting microorganisms. Examples of bacteria include those belonging to the genus Lactobacillus, the genus *Streptococcus*, the genus *Bacillus*, the genus *Leuconostoc*, and the genus *Pediococcus*. Examples of yeast include those belonging to the genus *Saccharomyces* and the genus *Kluyveromyces*. Examples of molds include those belonging to the genus *Rhyzopus* and the genus *Aspergillus*. As the lactic acid-fermenting microorganisms, microorganisms having the capacity for homolactic fermentation are particularly preferably used.

In the fermentation process, sugars contained in a medium (e.g., hexose or pentose) are metabolized and lactic acid is generated. During lactic acid fermentation, the pH level of fermentation solution is lowered due to the lactic acid generation. Thus, the fermentation solution is neutralized with the use of a base, such as ammonia. Ammonia is used in the form of an aqueous solution (aqueous ammonia). It is preferable that ammonia be added to maintain the pH level of the fermentation solution in the neutral region (preferably a pH between 5 and 7). Thus, lactic acid reacts with ammonia, ammonium lactate is generated, and a fermentation solution containing ammonium lactate (an ammonium lactate solution) is obtained. In the method for producing a lactic acid ester according to the present invention, the fermentation solution may be used in that state. Preferably, bacteria are separated from the fermentation solution obtained by the fermentation process by means of centrifugation, membrane separation, or the like. Specifically, the reaction solution that is used in the method for producing a lactic acid ester according to the present invention may be prepared by adding alcohol to an untreated fermentation solution. Alternatively, it may be prepared by adding alcohol to a fermentation solution from which bacteria have been removed.

In the method for producing a lactic acid ester according to the present invention, ammonium lactate that is contained in the fermentation solution prepared above is esterified. Preferably, the fermentation solution is concentrated prior to esterification. Lactic acid concentration in the concentrated fermentation solution is preferably between 70% and 85% by mass. Examples of means for concentrating a fermentation solution include a multiple-effect evaporator and a thin-film evaporator. When concentrating a fermentation solution, heating is preferably carried out at 140° C. or lower in order to avoid lactic acid racemization.

Esterification can be carried out by adding alcohol to a fermentation concentrate to prepare a reaction solution and heating the resulting reaction solution. Use of alcohol having 4 or more carbon atoms is preferable. Use of alcohol having 4 carbon atoms (C4 alcohol) or alcohol having 5 carbon atoms (C5 alcohol) is particularly preferable. Examples of C4 or C5 alcohols include n-butyl alcohol, isobutyl alcohol, t-butyl alcohol, n-amyl alcohol, sec-amyl alcohol, t-amyl alcohol, isoamyl alcohol, sec-amyl alcohol, active amyl alcohol, diethyl carbinol, and t-butyl carbinol.

The amount of alcohol added is preferably 1 to 10 times, and more preferably 1.5 to 4 times (moles basis), that of the lactic acid in the fermentation solution. In esterification, heating is preferably carried out at a temperature between 100° C. and 150° C., and preferably between 120° C. and 140° C. This heating results in esterification of lactic acid and ammonium lactate in the reaction solution and generation of a lactic acid ester. When butyl alcohol is used, for example, lactic acid and ammonium lactate are esterified by butyl alcohol, and butyl lactate is then generated.

In the method for producing a lactic acid ester according to the present invention, ammonia that remains in the reaction solution and ammonia that is generated in the reaction solution as a byproduct are eliminated to adjust the ammonia concentration to 1.0% by weight or lower in the reaction solution. In the method for producing a lactic acid ester according to the present invention, means and techniques for removing ammonia from the reaction solution are not particularly limited. An example of a technique that can be employed is a method of removing ammonia from the reaction solution with alcohol vapor (e.g., butanol vapor). In such a case, ammonia removal with the aid of alcohol vapor is carried out until the ammonia concentration in the reaction solution reaches 1.0% by weight or lower, and preferably 0.8% by weight or lower. As the ammonia concentration in the reaction solution is lowered, the equilibrium conversion rate of the esterification is increased. Disadvantageously, this may lead to an increased production cost due to an increase in input energy required for the removal of ammonia from the reaction solution. Accordingly, the ammonia concentration in the reaction solution is preferably 0.3% by weight or higher, and more preferably 0.5% by weight or higher.

Alcohol vapor that is discharged at the time of ammonia removal contains alcohol, water, and ammonia contained in the reaction solution. In the method for producing a lactic acid ester according to the present invention, preferably, ammonia and water contained in alcohol vapor are removed to purify alcohol, and the purified alcohol is returned into the reaction solution.

In the step of esterification, the reaction is preferably completed with a 50% to 90% conversion rate of equilibrium conversion rate of the esterification. It is not preferable to perform esterification until a conversion rate exceeding 90% of the equilibrium conversion rate is attained. This is because the reaction speed is gradually lowered, which results in a prolonged reaction time and increased equipment cost in the production process. When the reaction is completed with a 50% to 90% conversion rate of equilibrium conversion rate of the esterification, the reaction solution consequently contains unreacted lactic acid and ammonium lactate. However, the solution remaining after the recovery of a lactic acid ester from the reaction solution can be used as a reaction solution for esterification.

In the method for producing a lactic acid ester according to the present invention, a lactic acid ester is next recovered from the reaction solution. Means and techniques for recovering a lactic acid ester are not particularly limited, and conventional recovery means and techniques can be adequately employed. For example, the reaction solution after the completion of the reaction can be subjected to distillation to separate and recover the lactic acid ester.

In the method for producing a lactic acid ester according to the present invention, the ammonia concentration may be adjusted to 1.0% by weight or lower in the reaction solution at the time of ammonium lactate esterification, so that the equilibrium ester conversion rate of the esterification can be enhanced. Table 1 shows the correlation between the ammonia concentration in the reaction solution and the equilibrium ester conversion rate of the esterification. The values shown in Table 1 were obtained as a result of esterification, which was performed at 140° C. in a closed system (without the distillation of vapor) having a butanol/(lactic acid and ammonium lactate) molar ratio of 4.0 in the reaction solution.

TABLE 1

| Ammonia concentration | Equilibrium conversion rate |
| --- | --- |
| 0.3% by weight | 73.3% |
| 0.6% by weight | 68.5% |
| 0.9% by weight | 61.9% |
| 1.2% by weight | 57.1% |
| 1.4% by weight | 50.0% |
| 1.9% by weight | 40.7% |
| 3.0% by weight | 23.5% |

As is apparent from Table 1, the ammonia concentration of 1.0% by weight or lower in the reaction solution for esterification realizes a high equilibrium ester conversion rate of exceeding 60% of the esterification. (The equilibrium conversion rate is determined based on the molar fraction of reaction components and reaction products in theory.)

In such a case, it is not preferable to excessively lower the ammonia concentration in order to enhance the equilibrium conversion rate. When the reaction is performed with the addition of 2.9 kg of butanol to 1.4 kg of the fermentation concentrate, the amounts of vapor distillation in the reaction solution are set at three different levels, and changes in ammonia concentration during esterification at each level are observed. Table 2 and FIG. 3 each show the results thereof.

TABLE 2

| | Amount distilled | | |
| --- | --- | --- | --- |
| Time (hr) | 0.3 l/hr | 0.6 l/hr | 0.9 l/hr |
| 0 | 2.67% | 2.93% | 2.76% |
| 1 | 2.12% | 1.91% | 1.98% |
| 2 | 1.77% | 1.68% | 1.55% |
| 3 | 1.5% | 1.31% | 1.2% |
| 4 | 1.28% | 1.08% | 0.97% |
| 5 | 1.1% | 0.9% | 0.8% |

Figure 3:
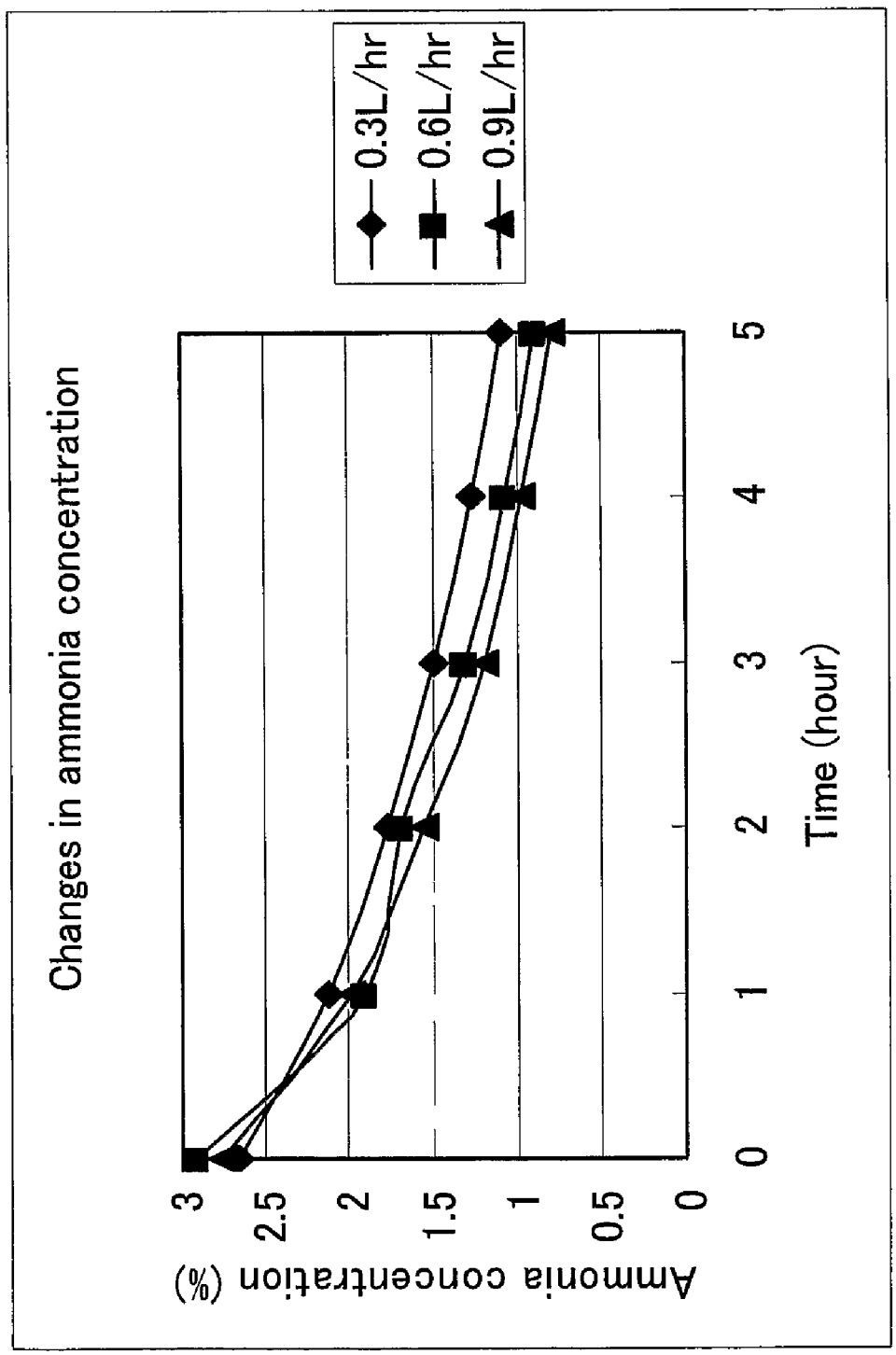
FIG. 3 shows a chart representing changes in ammonia concentration during esterification.

As shown in Table 2 and FIG. 3, a larger amount of vapor distilled (i.e., a larger input energy) results in a lower ammonia concentration, although the rate of such lowering is very low. Specifically, if the amount of vapor distilled is tripled from 0.3 l/hr to 0.9 l/hr, the ammonia concentration is lowered by approximately 20%. (In this case, the amount of butanol equivalent to the amount of vapor distilled is supplied to the reaction tank.) Accordingly, excessive lowering of the ammonia concentration by energy input for the purpose of enhancing the conversion rate results in increased amount of energy required for the generation of unit weight of a lactic acid ester. That is, such lowering results in increased cost. In the actual production process, a novel fermentation concentrate is mixed with an unreacted solution with a low ammonia concentration (i.e., a residual solution after esterification and distillation) to lower the ammonia concentration at the initial stage of the reaction. Thus, the reaction solution is obtained.

The ammonia concentration can be lowered by increasing the butanol/(lactic acid and ammonium lactate) molar ratio, however, such procedure is not preferable since the amount of a lactic acid ester generated per unit volume is reduced, and the equipment cost is increased. In the method for producing a lactic acid ester according to the present invention, it is preferable that ammonia is removed from alcohol vapor (e.g., butanol vapor) for removing ammonia, followed by the purified alcohol (butanol) is returned into the reaction solution. In such a case, the alcohol to be returned into the reaction solution does not contain ammonia. Thus, input energy required to adjust the ammonia concentration to 1.0% by weight or lower in the reaction solution is advantageously low. In the method for producing a lactic acid ester according to the present invention, accordingly, input energy required for the process of producing a lactic acid ester can be reduced.

In the method for producing a lactic acid ester according to the present invention, it is preferable that esterification be performed at a rapid reaction speed that is attained a 50% to 90% conversion rate of equilibrium conversion rate of the esterification. In this case, unreacted ammonium lactate can be refluxed to the reaction solution to improve the yield of the lactic acid ester while maintaining a rapid reaction speed. The method for producing a lactic acid ester of the present invention eliminates the need for the addition of sulfuric acid or the like, which had been carried out in conventional techniques. Therefore, chemical costs can be remarkably reduced.

As described above, it can be said that the method for producing a lactic acid ester of the present invention is an effective technique since input energy at the time of production can be minimized, chemical costs can be reduced, and equipment costs can be minimized. The application of the method for producing a lactic acid ester of the present invention enables the construction of a production line for industrially producing a lactic acid ester and lactic acid synthesized from a lactic acid ester in a cost-effective manner.

EXAMPLES

Hereafter, the present invention is described in greater detail with reference to the examples, although the technical scope of the present invention is not limited to the following examples.

Example 1

Example 1 concerns the production of a lactic acid ester with the use of the apparatus shown in FIG. 1. The apparatus shown in FIG. 1 comprises a reaction tank 1, which is capable of agitation with the aid of an agitation blade, a distillation tower 2, a condenser 3, a first condensate tank 4, a second condensate tank 5, and a vacuum pump 6.

At the outset, the pH level was adjusted with aqueous ammonia under aeration-agitation conditions, and lactic acid fermentation was carried out, in order to prepare an aqueous solution of ammonia lactate for this example.

Consequently, an aqueous solution containing approximately 12% ammonium lactate by weight was obtained. Subsequently, the aqueous solution was filtered through a microfiltration (MF) filter to separate bacteria, moisture was evaporated to concentrate the solution, and an aqueous solution containing approximately 70% lactic acid by weight (% by weight in lactic acid equivalent) was then prepared. The ammonia concentration was 8.0% by weight in the prepared fermentation concentrate. At the time of concentration, part of ammonia was evaporated, although it is possible to recover it as an aqueous solution and to recycle it.

In this example, the thus-prepared fermentation concentrate was loaded into reaction tank 1, and esterification was carried out. Specifically, 500 g of the prepared fermentation concentrate and 2,200 g of butanol were added to 475 g of the liquid remaining in reaction tank 1 after esterification and distillation (lactic acid concentration: 67% by weight) to prepare a reaction solution. The amount of butanol added was 4 times in terms of moles that of lactic acid and ammonium lactate contained in the reaction solution. The ammonia concentration in the reaction solution was 1.3% by weight.

Esterification was carried out for 4 hours by heating the reaction solution to 140° C. In this case, butanol vapor was distilled at 400 g/hr until the ammonia concentration was reduced to 0.8% by weight in the reaction solution. Butanol vapor was distilled over a period of 3 hours. Purified butanol was supplied to reaction tank 1 at the same speed as the speed of distillation of butanol vapor.

As a result of the esterification for 4 hours, the butyl lactate concentration was 18.9% by weight in the reaction solution, and the conversion rate of esterification was 55%. The reaction speed for the esterification was 0.29 mol/l·hr (where "l" used herein indicates the volume of the reaction solution at room temperature).

Subsequently, butanol was separated from the reaction solution after the esterification, and butyl lactate was then separated. The inside of reaction tank 1 was gradually depressurized to distill butanol vapor. Such distillation was performed until the temperature of the reaction solution in reaction tank 1 reached 120° C. and the inside of reaction tank 1 was depressurized to 50 hPa. Butanol vapor was recovered as a solution through distillation tower 2 and condenser 3. In order to prevent the simultaneous distillation of butyl lactate, part of the solution was refluxed to the reaction solution. Subsequently, the pressure in reaction tank 1 was gradually lowered, and butyl lactate was distilled at 120° C. to 20 hPa. As a result, 600 g of butyl lactate was recovered.

In the present example, the butyl lactate obtained by the method for producing a lactic acid ester according to the present invention was hydrolyzed to prepare an aqueous solution of lactic acid. Specifically, water was added in an amount 16 times that of the recovered butyl lactate by moles, the mixture was heated to 120° C., and the reaction was continued for 4 hours. Butanol resulting from hydrolysis was evaporated and distilled to the outside of the system with water. After the completion of the reaction, water vapor was further distilled, and an aqueous solution containing 90% lactic acid by weight was recovered in the end.

Example 2

Figure 2:
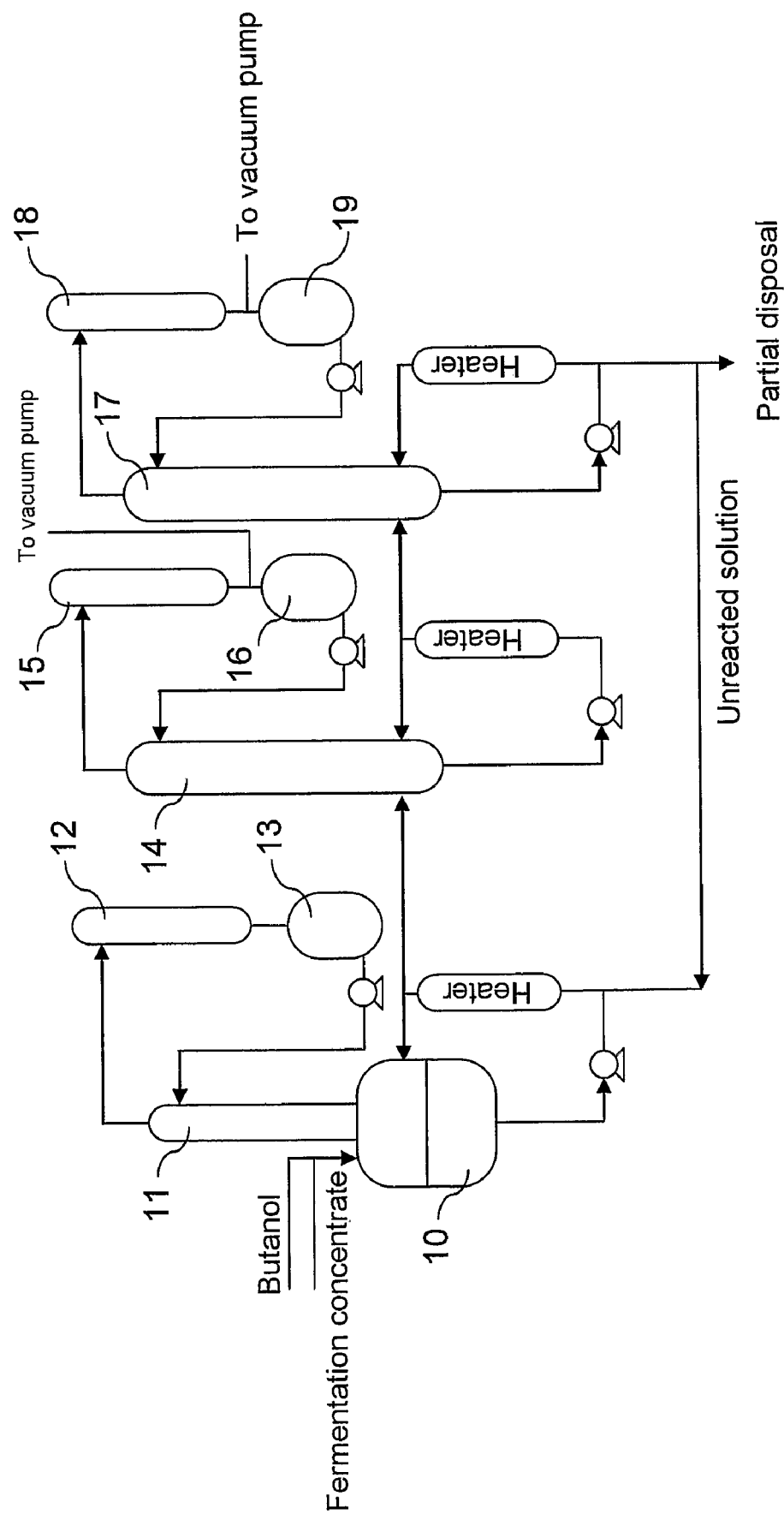
FIG. 2 shows another embodiment of the system for producing a lactic acid ester according to the present invention.

Example 2 concerns the production of a lactic acid ester with the use of the apparatus shown in FIG. 2. The apparatus shown in FIG. 2 comprises a reaction tank 10, a distillation tower 11 for adjusting the ammonia concentration, a condenser 12 connected to distillation tower 11, and a condensate tank 13 connected to distillation tower 11 and to condenser 12. The ammonia concentration in the reaction tank 10 is adjusted with the aid of distillation tower 11, condenser 12, and condensate tank 13. Also, the apparatus shown in FIG. 2 comprises a first distillation tower 14 for separating butanol from the reaction solution after the esterification, a condenser 15 connected to first distillation tower 14, and a condensate tank 16 connected to first distillation tower 14 and to condenser 15. Butanol is separated from the reaction solution after the reaction with the aid of first distillation tower 14, condenser 15, and condensate tank 16. Further, the apparatus shown in FIG. 2 comprises a second distillation tower 17 for separating butyl lactate from the reaction solution after the esterification, a condenser 18 connected to second distillation tower 17, and a condensate tank 19 connected to first distillation tower 17 and to condenser 18. Butyl lactate is separated from the reaction solution after the reaction with the aid of second distillation tower 17, condenser 18, and condensate tank 19.

In this example, a fermentation concentrate was prepared in the same manner as in Example 1. Also, esterification was carried out while distilling ammonia-containing butanol vapor so as to bring the ammonia concentration in reaction tank 10 to 1.0% by weight or lower with the aid of distillation tower 11, condenser 12, and condensate tank 13. With the use of the apparatus explained in this example, the fermentation concentrate and butanol were continuously supplied to reaction tank 10. Simultaneously, the reaction solution was successively supplied from reaction tank 10 to first distillation tower 14. According to apparatus of this example, butanol was separated with the aid of first distillation tower 14, butyl lactate contained in the reaction solution was separated with the aid of a second distillation tower 17 and a condenser 18, and butyl lactate was recovered in a condensate tank 19. Furthermore, butyl lactate was separated and introduced into condensate tank 19 with the aid of second distillation tower 17 and condenser 18, and part of the reaction solution containing unreacted lactic acid was refluxed to reaction tank 10. In this case, part of the reaction solution containing unreacted lactic acid was discarded to inhibit the accumulation of impurities in reaction tank 10.

In Example 2, an aqueous solution of lactic acid was recovered by hydrolyzing butyl lactate in the same manner as in Example 1.

INDUSTRIAL APPLICABILITY

According to the method for producing a lactic acid ester of the present invention, input energy at the time of production can be minimized, chemical costs can be reduced, and equipment costs can be minimized. Thus, a lactic acid ester can be produced at low cost.

The invention claimed is:

1. A method for producing a lactic acid ester comprising:
    performing an esterification reaction in a reaction solution containing ammonium lactate obtained via fermentation and alcohol comprising adjusting the ammonia concentration in the reaction solution to an ammonia concentration of between 0.3% and 0.8% by weight; and
    recovering the lactic acid ester synthesized in the esterification reaction wherein the esterification reaction is completed at a conversion rate that is 50% to 90% of the equilibrium conversion rate of the esterification reaction.

2. The method for producing a lactic acid ester according to claim 1, wherein the ammonia contained in the reaction solution is discharged to the outside of the reaction system with butanol vapor.

3. The method for producing a lactic acid ester according to claim 1, wherein at least some of the liquid remaining after the recovery of the lactic acid ester is reacted with additional reaction solution.

* * * * *